United States Patent [19]

Szejtli et al.

[11] Patent Number: 4,518,588

[45] Date of Patent: May 21, 1985

[54] PROCESS FOR THE PREPARATION OF AN INCLUSION COMPLEX OF N-(1-PHENYLETHYL)-3,3-DIPHENYLPROPYLAMINE AND THE HYDROCHLORIDE THEREOF RESPECTIVELY WITH CYCLODEXTRIN

[75] Inventors: József Szejtli; Ágnes Stadler née Szóke; Mária Vikmon née Király; Dezsó Korbonits; Sándor Virág; István Turcsán; Pál Kiss, all of Budapest, Hungary

[73] Assignee: CHINOIN Gyogyszer es Vegyeszeti Termekek Gyara Rt., Budapest, Hungary

[21] Appl. No.: 456,029

[22] PCT Filed: May 12, 1982

[86] PCT No.: PCT/HU82/00024

§ 371 Date: Dec. 22, 1982

§ 102(e) Date: Dec. 22, 1982

[87] PCT Pub. No.: WO82/04052

PCT Pub. Date: Nov. 25, 1982

[30] Foreign Application Priority Data

May 12, 1981 [HU] Hungary .............................. 1286-81

[51] Int. Cl.$^3$ .................. A61K 31/73; C08B 37/16
[52] U.S. Cl. .................................. 514/58; 536/46; 536/103
[58] Field of Search ................. 424/180, 361; 536/46, 536/103

[56] References Cited

U.S. PATENT DOCUMENTS 3,553,191  1/1971  Parmerter et al. .................... 536/46
4,407,795  10/1983  Nicolau et al. ....................... 536/46

FOREIGN PATENT DOCUMENTS 8200024  11/1982  Hungary ............................. 536/103

Primary Examiner—Johnnie R. Brown
Attorney, Agent, or Firm—Karl F. Ross; Herbert Dubno

[57] ABSTRACT

An inclusion complex is disclosed of N-(1-phenylethyl)-3, 3-diphenyl-propylamine or its hydrochloride complexed with a cyclodextrin as well as a process for the preparation thereof and pharmaceutical compositions containing same. The new inclusion complexes have coronary dilatory activity and have greater water soluble than simple N-(1-phenylethyl)-3, 3-diphenyl-propyl amine or the hydrochloride thereof.

19 Claims, 2 Drawing Figures

4,518,588

PROCESS FOR THE PREPARATION OF AN INCLUSION COMPLEX OF N-(1--PHENYLETHYL)-3,3-DIPHENYLPROPYLAMINE AND THE HYDROCHLORIDE THEREOF RESPECTIVELY WITH CYCLODEXTRIN

FIELD OF THE INVENTION

The invention relates to the preparation of an inclusion complex of N-(1-phenylethyl)-3,3-diphenylpropylamine or the hydrochloride thereof with cyclodextrin.

The inclusion complex can be prepared by reacting N-(1-phenylethyl)-3,3-diphenylpropylamine base or the hydrochloride thereof with cyclodextrin under stirring at 4°-60° C. in an aqueous and/or ethanolic medium and optionally treating the obtained complex of the base with hydrochloric acid.

BACKGROUND OF THE INVENTION

N-(1-phenylethyl)-3,3-diphenylpropylamine (referred to hereinafter as phendiline), is a coronary dilator calcium antagonist (see Hungarian Pat. No. 150 534). The substance is an oily liquid and its hydrochloride salt is used as an active ingredient of a pharmaceutical composition known under the trade name Sensit. A solid pharmaceutical composition can be prepared only from the hydrochloride. However, phendiline hydrochloride is an extremely hydrophobic substance. Thus the rate and extent of the resorption of phendiline are not satisfactory.

OBJECT OF THE INVENTION

The object of the invention is to provide a process by which phendiline or its hydrochloride can be prepared in a form which is more soluble and thus its in vivo resorption can be accelarated and increased.

DESCRIPTION OF THE INVENTION

We have now found that if phendiline or its hydrochloride is converted to a cyclodextrin inclusion complex the obtained complex is much more soluble at a pH and temperature corresponding to these of gastric acid than is the original molecule. The rate and extent of the dissolution are increased.

Cyclodextrin molecules are known to have a cylindric structure, the inner surface of which is apolar and thus they are capable of binding hydrophobic molecules in the form of an inclusion complex. Such hydrophobic molecules may in the present case be phendiline or its hydrochloride, the solubility of which in water is very poor. Our experiments have shown that when reacting phendiline with cyclodextrins, two molecules of cyclodextrin form an inclusion complex with each molecule of phendiline, which surprisingly loses one of its cyclodextrin molecules in an aqueous hydrochloric acid solution corresponding to the pH of gastric acid and the complex is readily converted to a molecularly dispersed state. The solubility is thus increased and a better biological activity can be observed. When stirring cyclodextrins vigorously with phendiline in an aqueous and/or ethanolic medium, the phendiline molecule displaces the water molecules in the hollow of the cyclodextrin and due to the formed apolar-apolar interaction an inclusion complex is formed.

This intensive dissolution process for the product of molecular encapsulation by cyclodextrins, combined with salt formation and partial release of cyclodextrin is new. The essence of the process is that the host molecule is ionized in the cyclodextrin inclusion complex of the non-ionic molecule, and due to the formation of the ionic bond the appearing intensive charge and the accompanying intensive hydrated state casts off part of the cyclodextrin casing of the host molecule. If an inclusion complex of a non-ionic host molecule which is not well soluble in water and which has a crystalline grid structure is thus converted to the ionic state, then the crystal granule disintegrates explosively and the entire amount of substance is transformed to molecularly dispersed state, i.e. to a solution.

The resulting, molecular structure is relatively highly soluble as its one end is hydrated due to the ionized state and its other end—which is apolar to a great extent and causes thus a poor solubility of the molecule—is covered from the outside by a hydrophilic cyclodextrin ring.

Phendiline is not soluble in water, but even the solubility of its hydrochloride is extremely poor. If the free base is treated with hydrochloric acid, then the hydrophobic hydrochloride on the surface of the oil drops of the base not only inhibits the dissolution but further salt formation as well. If one molecule of phendiline forms an inclusion complex with two molecules of cyclodextrin, a crystalline product is obtained which itself is relatively not highly soluble in water.

If, however this inclusion complex is introduced into an acidic medium, such as gastric acid, then the nitrogen atom of the phendiline takes up a proton and becomes ionic, breaking off the cyclodextrin ring close to the nitrogen atom. As a result a structure is formed in which the ionic phenylethylamino part of the phendiline is free, predominantly hydrated, and the apolar diphenylpropyl group remains in a complex with one molecule of cyclodextrin. A 2:1 complex is thus converted to a 1:1 complex in in acidic medium, when the phendiline cyclodextrin complex is mixed with an acid, and the product is transformed into a molecularly dispersed state, i.e. is dissolved.

Both the phendiline hydrochloride monocyclodextrin complex and the phendiline monocyclodextrin complex are highly soluble in water. Thus both the 2:1 molar complex of the basis form (active ingredient content about 11%), and the 1:1 molar complex of the hydrochloride (active ingredient content on an average 21%) show an increased solubility compared to that of phendiline hydrochloride and because of the biological activity these complexes are suitable for the preparation of pharmaceutical compositions.

In order to demonstrate biological activity we examined the effect of the inclusion of the active ingredient into an inclusion complex with cyclodextrin upon the dissolution and resorption of phendiline and phendiline hydrochloride under in vitro circumstances. The in vitro tests were justified by the fact that the measurements are much more reproducible than by carrying out the tests in vivo.

The dissolution and the resorption are subsequent processes which depend greatly on each other. Under physiological conditions resorption is partially influenced by the pH relations at the place of the resorption and partially by the time spent by the pharmaceutical at the place of the resorption.

The average spent time in each segment of the gastro-intestinal system and the pH values are as follows:

| in the stomach | 0–30 min | pH = 1.2 |
|---|---|---|
| at the beginning of the small intestine | 30–60 min | pH = 5–6 |
| in the further segment of the small intestine | 60–360 min | pH = 6–7 |

The tests were carried out accordingly.

The resorption tests were performed on a Sartorius SM 16750 Resorption model, the membranes used were suitable for modelling the resorption from the stomach and from the intestine. On the basis of the test results the diffusion ($K_d$) and the resorption rate constant ($K_i$) were calculated for the test substances. The results are summarized in the following table.

| Substance | $K_d$ [cm$^2$ min$^{-1}$] | $K_i$ [min$^{-1}$] |
|---|---|---|
| | from the intestine | |
| Phendiline | $6.9 \times 10^{-4}$ | $5.1 \times 10^{-3}$ |
| Phendiline-$\beta$-cyclo-dextrin-complex | $1.42 \times 10^{-3}$ | $1.24 \times 10^{-2}$ |
| Phendiline-hydrochloride | $6.7 \times 10^{-4}$ | $4.9 \times 10^{-3}$ |
| Phendiline-hydrochloride-$\beta$-cyclodextrin-complex | $1.71 \times 10^{-3}$ | $1.52 \times 10^{-2}$ |

Both $K_d$ and $K_i$ are more than 100% higher in case of resorption from the intestine as a consequence of the complex formation.

The determination of the dissolved ($M_G$) and the resorbed ($M_i$) active ingredient was performed on a Sartorius SM 16751 type Löse model [H. Stricker: Pharm. Ind. 33, 157 (1971); H. Sticker: Drugs in Germany 14, 93 (1971)].

Figure 1:
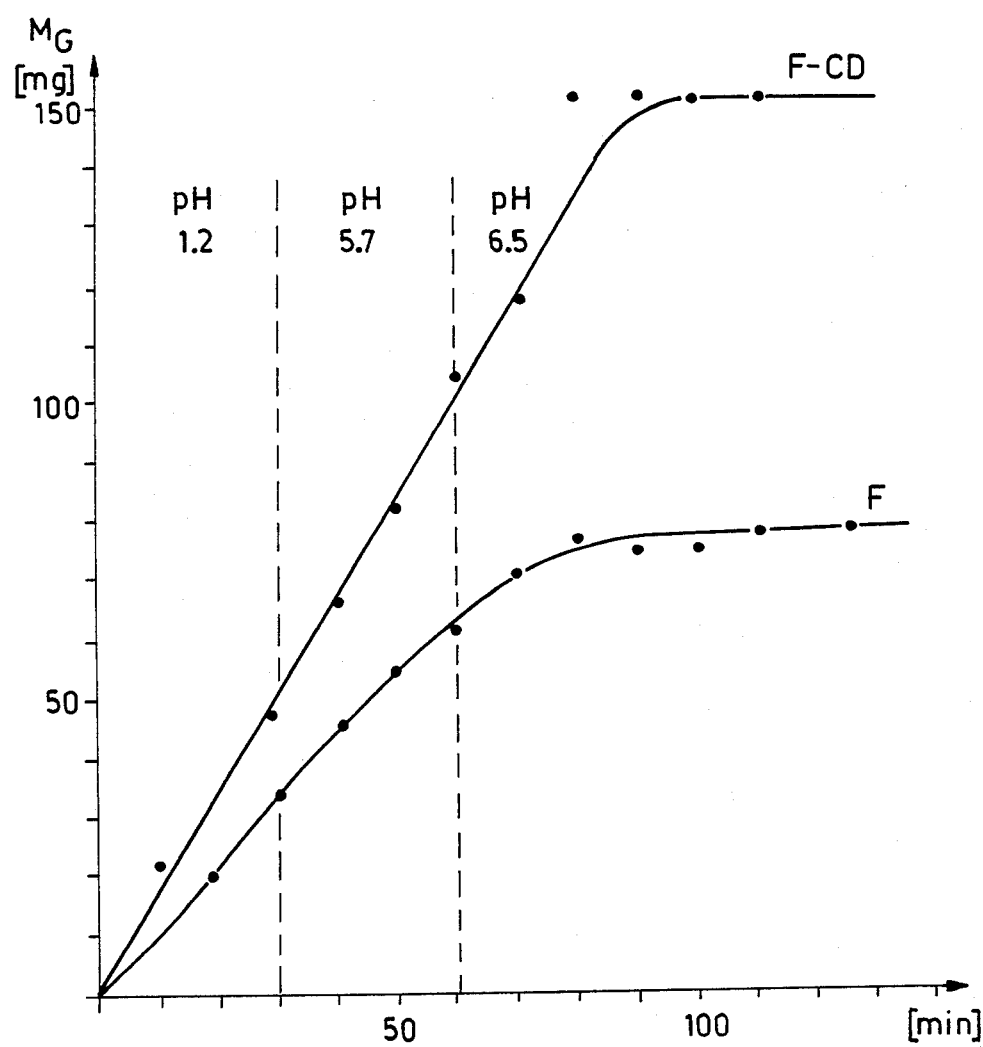
FIGS. 1 and 2 are graphs illustrating the specific examples.

FIG. 1 shows the dissolution of phendiline and phendiline cyclodextrine complex in some segments of the gastro-intestinal system over a time period where F stands for the dissolution of phendiline and F-CD stands for the dissolution of the phendiline-cyclodextrin complex.

In the 100. minute 75 mg. phendiline base were dissolved whereas the amount of the dissolved phendiline-CD-complex amounted to 150 mg.

Figure 2:
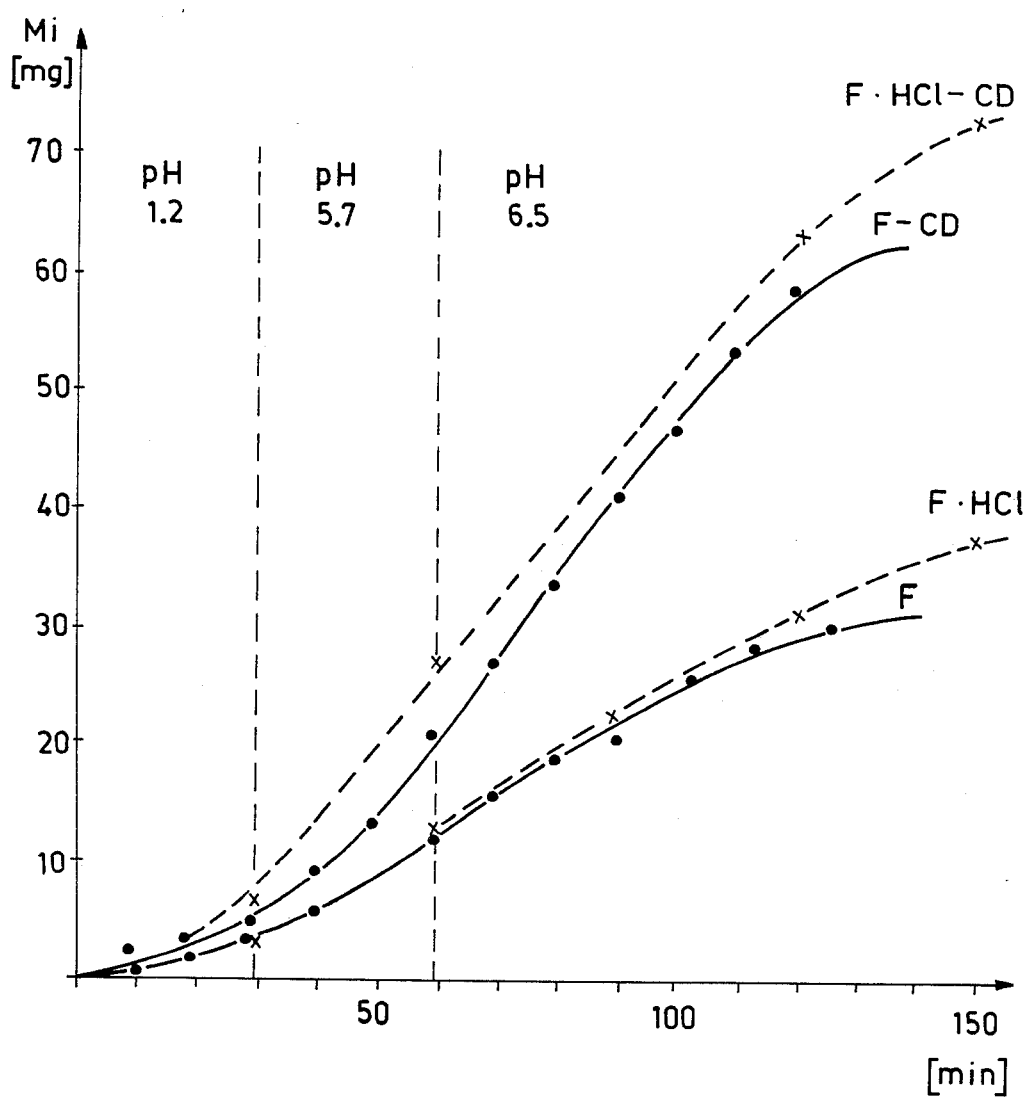

The amount of the resorbed phendiline, phendiline-CD-complex as well as phendiline hydrochloride and phendiline-hydrochloride-CD-complex from the gastro-intestinal tract is shown in FIG. 2 where F stands for the resorbed amount of phendiline, F-CD stands for the resorbed amount of phendiline-cyclodextrine-complex, FHCl stands for the resorbed amount of phendiline-hydrochloride and FHCl-CD stands for the resorbed amount of phendiline-hydrochloride-cyclodextrine-complex.

Similarly to the increased dissolution values obtained both in the case of the base and the salt, the amount of the resorbed active ingredient from the intestinal tract doubled as a result of the complex formation. Thus the same activity can be achieved by only a half dosage.

In the toxicological tests we examined the acute toxicity of phendiline, phendiline-cyclodextrine-complex, and phendiline-hydrochloride and phendiline-hydrochloride-cyclodextrine-complex in mice intraperitoneally. The test substances were administered to 10 male and 10 female animals in each group by means of 5% Tween 80. The doses were calculated in the case of the complexes on the basis of the amount of phendiline active ingredient. The test results are summarized in the following table.

| | Observation time (hours) | LD$_{50}$ (mg./kg.) |
|---|---|---|
| Intraperitoneal administration | | |
| phendiline | 24 | 47.54 |
| phendiline-cyclo-dextrine-complex | 24 | 157.47 |
| phendiline-hydrochloride | 1 | 81.14 |
| phendiline-hydrochloride-CD-complex | 1 | 160.55 |
| Per os administration | | |
| phendiline | 72 | 512.41 |
| phendiline-CD-complex | 72 | 624.65 |
| phendiline-hydrochloride | 24 | 522.24 |
| phendiline-hydrochloride-CD-complex | 24 | 954.88 |

The phendiline cyclodextrin complexes according to the invention are white powdery microcrystalline substances, which can be utilized in the form of pharmaceutical compositions. The pharmaceutical compositions contain an effective amount of the cyclodextrinphendiline inclusion complex optionally admixed with pharmaceutically acceptable organic or inorganic carriers. The most suitable forms may be tablets, dragées, capsules, syrups. These compositions contain the active ingredient admixed with diluents, such as lactose, dextrose, sucrose, glycine and/or lubricants, such as siliceous, earth, talc, stearic acid and salts thereof, polyethylene glycol, binding agents, filling agents, dyes, flavoring agents. The compositions may contain further biologically active components. The compositions may be prepared by methods known per se, such as mixing, granulating, preparing dragées by coating. The active ingredient content of the compositions may vary from 10 to 40%. The dosage depends on various factors, such as the route of administration, the state and age of the patient, etc.

The details of the invention are further demonstrated in the following Examples which merely serve for illustration and not for limitation.

EXAMPLE 1

10 g. (7.5 mmoles) of $\beta$-cyclodextrin containing 15% water are suspended in 40 ml. of water at room temperature whereafter 0.96 g. (3 mmoles) of phendiline in 2 ml. of 96% by volume are added dropwise under vigorous stirring. The suspension is then stirred for another 5 hours, filtered and dried. 9.2 g. of air-dried phendiline-$\beta$-cyclodextrin complex are obtained. Phendiline content: 9.7% by weight. The product is a white powder without a characteristic melting point. Determination of the phendiline content of the complex: 0.05 g. of the product is dissolved in 25 ml. of 50% by volume of ethanol and it is subjected to photometry at wavelength 258 nm against 50% by volume ethanol. The phendiline content is determined by means of a calibration curve.

EXAMPLE 2

26.8 g. (20 mmoles) of $\beta$-cyclodextrin containing 15% water are dissolved in a mixture of 350 ml. of water and 50 ml. of ethanol of 96 $\beta$ by volume at 60° C. and a mixture of 3.15 g. (10 mmoles) of phendiline and 40 ml. of 96% by volume of ethanol are added within 30 minutes under vigorous stirring. The mixture is cooled to room temperature within 6 hours and allowed to stand overnight at +4° C. The precipitated crystals are filtered, and air dried. Thus 28.4 g. of phendiline β-cyclodextrin complex are obtained, phendiline content: 10.7% by weight.

EXAMPLE 3

13.3 g of β-cyclodextrine (10 mmoles) containing 15% humidity are suspended in 10 ml. of distilled water in a mortar. A solution of 1.55 g. (5 mmoles) of phendiline in 5 ml. 96% by volume of ethanol is added. A diluted suspension is obtained which is homogenized under steady trituration. After about thirty minutes the suspension becomes ointment like and the obtained substance is placed to an exsiccator and dried above phosphorous pentoxide for 24 hours. The solid complex which is free of solvent and water traces is pulverized. 12.5 g. of phendiline β-cyclodextrin complex are obtained, phendiline content: 11.8%.

EXAMPLE 4

2.1 g. (1.4 mmole) of γ-cyclodextrin containing 15% of water are dissolved in 15 ml. of water at 40° C. A mixture of 0.158 g. (0.5 mmole) of phendiline and 1 ml. of 96% by volume ethanol is added dropwise under stirring. The crystals start to precipitate during the addition. The suspension is cooled to room temperature within 2 hours and stored at +4° C. overnight. After filtration and air drying 0.66 g. of phendiline-γ-cyclodextrin complex is obtained, phendiline content: 11.3% by weight.

EXAMPLE 5

1.0 g. (1.0 mmole) of α-cyclodextrin is dissolved at 40° C. in 7 ml. of distilled water. A mixture of 0.158 g. (0.5 mmole) phendiline in 1 ml. of 96% by volume ethanol is added dropwise under stirring. The crystals start to precipitate during the addition. The suspension is cooled to room temperature within 2 hours, stored overnight at +4° C., filtered and dried. 0.5 g. of phendiline-α-cyclodextrin complex is obtained, containing 12.2% by weight of phendiline.

EXAMPLE 6

1.8 g. of a cyclodextrin mixture containing 11% water (dry substance content according to high pressure liquid chromatography: 70% β-cyclodextrin, 20% γ-cyclodextrin, 10.4% α-cyclodextrin, average molecular weight: 1151, mmoles: 1.4) are dissolved in a mixture of 20 ml. of distilled water and 3 ml. of 96% by volume of ethanol at 60° C. A mixture of 0.22 g. (0.7 mmole) of phendiline and 2 ml. of 96% by volume of ethanol are added dropwise under vigorous stirring. The mixture is cooled to room temperature within 3 hours and allowed to stand at +4° C. overnight. The precipitated crystalline product is filtered and air-dried. 1.3 g. of product are obtained, phendiline content: 11% by weight.

EXAMPLE 7

4 g. of β-cyclodextrin (3 mmoles) containing 15% of water are dissolved in 35 ml. of water at 60° C. A solution of 1.05 g. (3 mmoles) of phendiline hydrochloride in 8 ml. of 96% by volume ethanol is added dropwise. The mixture is cooled to room temperature within 5 hours, and allowed to stand overnight at +4° C. The precipitated white crystalline product is filtered and dried. The air-dried phendiline-β-cyclodextrin complex amounts to 3.8 g., containing 22.2% by weight of phendiline hydrochloride.

EXAMPLE 8

13.4 g. (10 mmoles) of β-cyclodextrin containing 15% water are dissolved in a mixture of 160 ml. of water and 10 ml. of 1N hydrochloric acid at 50° C. A solution of 3.15 g. (10 mmoles) of phendiline in 30 ml. of 96% by volume ethanol is added. The mixture is cooled to room temperature within 4 hours and allowed to stand overnight at +4° C. The precipitated crystalline substance is filtered and dried. 11.2 g. of phendiline-hydrochloride-β-cyclodextrin complex are obtained. Phendiline-hydrochloride content: 20.5% by weight.

EXAMPLE 9

5.0 g. of phendiline-β-cyclodextrin complex prepared according to Example 2 (phendiline content: 10.7% by weight) are dissolved in a mixture of 35 ml. of water and 2 ml. of 1N hydrochloric acid at 37° C. The solution is allowed to stand for 24 hours at room temperature and the precipitated crystalline substance is filtered. 2.0 g. of air-dried phendiline hydrochloride β-cyclodextrin are obtained, phendiline content: 21.2% by weight.

EXAMPLE 10

Roentgen diffraction assay to prove that according to Example 1 a complex was obtained.

The roentgen diffraction powder diagrams of β-cyclodextrin and phendiline-β-cyclodextrin complex show that the characteristic reflexion peaks appear at significantly different 2θ° angle values proving the different crystal structures. As the molecule enclosed to complex is liquid the different crystal structures proves the complex formation.

Thermoanalytical assay of the product according to Example 1.

The thermoanalytical assay shows characteristic differences between the phendiline-β-cyclodextrin complex and the physical mixture of phendiline and β-cyclodextrin complex. Phendiline starts to evaporate respectively to decompose at 150° C. and 98% mass change can be observed up to 250° C.

Cyclodextrin decomposes at 270° C. and at 300° C. β-cyclodextrin melts with decomposition.

The physical mixture looses its cyclodextrin water content at 100° C., and at 150° C. to 250° C. its phendiline content. The active ingredient is released from the complex only when the cyclodextrin decomposes i.e. at 270° to 300° C.

The thermoanalytical assay also shows that phendiline and β-cyclodextrin form a complex at a molar ratio of 1:2. In case of phendiline excess the excess phendiline behaves like in a physical mixture, i.e. the decomposition starts already at 150° to 250° C.

EXAMPLE 11

Assay of solubility of phendiline hydrochloride β-cyclodextrin complex prepared according to Example 7.

Phendiline hydrochloride β-cyclodextrin complex corresponding to 200 mg. phendiline active ingredient are dissolved at 37° C. and stirred by a magnetic stirrer at 150 rot./min. The active ingredient content of the samples is determined by spectrophotometry.

The following table summarizes the results of the dissolution rate assay:

| Time minutes | phendiline hydrochloride β-cyclodextrin complex phendiline conc. mg./ml. |
| --- | --- |
| 1 | 13.3 |
| 5 | 12.7 |
| 15 | 12.9 |
| 30 | 12.8 |
| 60 | 13.3 |
| 120 | 14.6 |

0.22 g. (0.6 mmole) of phendiline hydrochloride is stirred at 37° C. for 3 hours in 3 ml. of water and in β-cyclodextrin solutions of various concentration by a magnetic stirrer at 150 rot./min rate. The concentration of the dissolved phendiline hydrochloride is determined by spectrophotometry and expressed in phendiline equivalents. The test results are summarized as follows:

| β-cyclodextrin concentration | | phendiline concentration | | β-cyclodextrin mmole |
| --- | --- | --- | --- | --- |
| mg./ml. | mmole/l. | mg./ml. | mmole/l. | phendiline mmole |
| 15 | 13.2 | 4.39 | 13.9 | 0.95 |
| 20 | 17.6 | 5.95 | 18.6 | 0.95 |
| 25 | 22.0 | 6.94 | 22.0 | 1.00 |
| 30 | 26.4 | 7.51 | 23.8 | 1.10 |

The molar ratio values of β-cyclodextrin mole/phendiline mole in the last column of the table shows that phendiline hydrochloride forms substantially an 1:1 complex with β-cyclodextrin.

EXAMPLE 12

Preparation of tablets containing phendiline β-cyclodextrin complex according to Example 3.

| | |
| --- | --- |
| phendiline-β-cyclodextrin complex | 398 g. |
| magnesium stearate | 5 g. |
| colloidal silicic acid | 7 g. |
| microcrystalline cellulose (Avicel PH 102) | 90 g. |

The above substances are mixed together, homogenized and tablets of an average weight of 500 mg. and diameter of 13 mm. are compressed from the powder mixture. The tablets contain on an average about 45 mg. of phendiline corresponding to 50 mg. of phendiline hydrochloride. This tablet contains an equivalent amount of active ingredient to a tablet containing 50 mg. of phendiline hydrochloride.

EXAMPLE 13

Preparation of a suspension syrup from phendiline-β-cyclodextrin according to Example 3.

| | |
| --- | --- |
| phendiline-β-cyclodextrin complex | 5 g. |
| methyl-p-oxy-benzoate | 0.1 g. |
| aroma | 0.5 g. |
| carboxymethyl cellulose sodium | 0.9 g. |
| microcrystalline cellulose (Avicel RC) | 1.1 g. |
| sorbitol | 35 g. |
| distilled water | ad 100 ml. |

Carboxymethyl cellulose sodium is dissolved in about a half volume of water, the microcrystalline cellulose is dissolved in the solution and after swelling of the cellulose the phendiline β-cyclodextrin complex is admixed to the solution. Methyl-p-oxybenzoate, the aroma and sorbitol are dissolved in the remaining water and the obtained solution is added to the suspension prepared above. The volume of the suspension is filled up to 100 ml. and homogenized.

We claim:
1. A process for the preparation of inclusion complexes of N-(1-phenylethyl)-3,3-diphenylpropylamine or its hydrochloride with cyclodextrin, which comprises reacting N-(1-phenylethyl)-3,3-diphenylpropylamine base or hydrochloride thereof with cyclodextrin in an amount of 1 to 3 mmoles of the cyclodextrin per mmole of N-(1-phenylethyl)-3,3-diphenylpropylamine or its hydrochloride, under stirring at 4° to 60° C. in aqueous or ethanolic medium.

2. A process as claimed in claim 1 which comprises using N-(1-phenylethyl)-3,3-diphenylpropylamine and cyclodextrin at a molar ratio of 1:3.

3. A process as claimed in claim 1 which comprises using N-(1-phenylethyl)-3,3-diphenylpropylamine and cyclodextrin at a molar ratio of 1:1.

4. A process as claimed in claim 1 which comprises using N-(1-phenylethyl)-3,3-diphenylpropylamine-hydrochloride and cyclodextrin at a molar ratio of 1:1.

5. A process as defined in claim 1 which comprises performing the reaction in aqueous medium in the presence of 1-20 ml. of water to 1 mmole of cyclodextrin.

6. A process as defined in claim 1 which comprises conducting the reaction in 5-32% by volume of aqueous-ethanolic medium.

7. A process as claimed in claim 1, which comprises reacting N-(1-phenylethyl)-3,3-diphenylpropylamine with cyclodextrin.

8. A process as claimed in claim 1, which comprises reacting N-(1-phenylethyl)-3,3-diphenylpropylamine hydrochloride with cyclodextrin.

9. A process as claimed in claim 1, which comprises using hydrochloride of N-(1-phenylethyl)-3,3-diphenylpropylamine formed in situ in the complex formation.

10. A process as claimed in claim 1, which comprises using α-cyclodextrin as cyclodextrin.

11. A process as claimed in claim 1, which comprises using β-cyclodextrin as cyclodextrin.

12. A process as claimed in claim 1, which comprises using γ-cyclodextrin as cyclodextrin.

13. Coronary dilatator calcium antagonist pharmaceutical compositions containing as active ingredient a pharmaceutically effective amount of either N-(1-phenylethyl)-3,3-diphenylpropylamine-hydrochloride cyclodextrin complex or N-(1-phenylethyl)-3,3-diphenylpropylamine-cyclodextrin complex admixed with a pharmaceutically acceptable carrier.

14. N-(1-phenylethyl)-3,3-diphenylpropylamine-α-cyclodextrin complex as defined in claim 1.

15. N-(1-phenylethyl)-3,3-diphenylpropylamine-β-cyclodextrin complex as defined in claim 1.

16. N-(1-phenylethyl)-3,3-diphenylpropylamine-γ-cyclodextrin complex as defined in claim 1.

17. N-(1-phenylethyl)-3,3-diphenylpropylamine hydrochloride β-cyclodextrin complex as defined in claim 1.

18. An inclusion complex of N-(1-phenylethyl)-3,3-diphenylpropylamine or its hydrochloride complexed with a cyclodextrin selected from the group which consists of a α-cyclodextrin, β-cyclodextrin and γ-cyclodextrin.

19. A coronary dilatative calcium antagonist method of treatment which comprises administering to a susceptible subject an effective amount of a composition consisting essentially of N-(1-phenylethyl)-3,3-diphenylpropylamine or its hydrochloride complexed with at least one cyclodextrin selected from the group which consists of α-cyclodextrin, β-cyclodextrin and γ-cyclodextrin.

* * * * *